United States Patent
Jin et al.

(10) Patent No.: US 7,774,425 B2
(45) Date of Patent: Aug. 10, 2010

(54) CONTENT MANAGEMENT METHOD AND APPARATUS

(75) Inventors: Ho Jin, Yongin-si (KR); Jung-yon Cho, Suwon-si (KR); Tae-young Song, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 614 days.

(21) Appl. No.: 11/640,278

(22) Filed: Dec. 18, 2006

(65) Prior Publication Data

US 2008/0016177 A1 Jan. 17, 2008

(30) Foreign Application Priority Data

Jul. 13, 2006 (KR) ........................ 10-2006-0065900

(51) Int. Cl.
*G06F 13/00* (2006.01)
(52) U.S. Cl. ...................................... 709/217
(58) Field of Classification Search ................. 709/217, 709/218, 223, 203–205, 250
See application file for complete search history.

(56) References Cited

U.S. PATENT DOCUMENTS

| 2006/0129917 | A1 | 6/2006 | Volk et al. | |
| 2006/0248209 | A1* | 11/2006 | Chiu et al. | 709/231 |
| 2006/0265503 | A1* | 11/2006 | Jones et al. | 709/227 |
| 2006/0265637 | A1* | 11/2006 | Marriott et al. | 715/500.1 |
| 2007/0077921 | A1* | 4/2007 | Hayashi et al. | 455/414.1 |
| 2007/0078714 | A1* | 4/2007 | Ott et al. | 705/14 |
| 2007/0078884 | A1* | 4/2007 | Ott et al. | 707/102 |
| 2008/0005347 | A1* | 1/2008 | Ott | 709/231 |

FOREIGN PATENT DOCUMENTS

| KR | 10-2004-0055450 A | 6/2004 |
| KR | 10-2005-0097741 A | 10/2005 |
| KR | 10-2006-0006050 A | 1/2006 |
| KR | 10-0573037 A | 4/2006 |
| WO | WO 2006/034384 A1 | 3/2006 |

OTHER PUBLICATIONS

Anonymous, Armangil's Podcatcher, May 19, 2005, Internet, Aug. 31, 2006, <http://podcatcher.rubyforge.org/>.

* cited by examiner

*Primary Examiner*—Robert B Harrell
(74) *Attorney, Agent, or Firm*—Sughrue Mion, PLLC

(57) ABSTRACT

A content management method and apparatus are provided. A method for a first device to provide content to a second device in a home network includes: receiving content information through a Really Simple Syndication (RSS) feed provided from a content server outside of the home network; updating a content list, which can be provided by the first device through the home network, based on the content information which is received; and transmitting the updated content list to the second device.

13 Claims, 9 Drawing Sheets

FIG. 3

```
<?xml version="1.0" encoding="eud-kr"?>
<rss version = "2.0">
    <channel>
    <title> SAMSUNG RSS</title>
    <link>http://www.sec.cr.kr/RSS</link>
    <description> Recent RSS Information </description>
    <language>ko</language>
    <lastBuildDate>Mar, 14 2006 09:10:50 GMT </lastBuildDate>
        <item> <title> VOD of RSS </title>
            <link>http://www.sec.co.kr/RSS/VOD</link>
            <author> Samsung </author>
            <pubDate>Mar, 15 2006 09:10:50 GMT </pubDate>
            <category> Internet Tech </category>
            <enclosure url="http://www.sec.co.kr/RSS/VOD/rssInfo.mpeg2" length="12216350" type="video/mpeg" />
        </item>
    ...
    </channel>
</rss>
```

FIG. 4

```
<DIDL-Lite
xmlns:dc="http://purl.org/dc/elements/1.1/"
xmlns:upnp="urn:schemas-upnp-org:metadata-1-0/upnp/"
xmlns="urn:schemas-upnp-org:metadata-1-0/DIDL-Lite/">
        <item id="5" parentID="3" restricted="false">
                <dc:title>Would</dc:title>
                <dc:creator>Alice In Chains</dc:creator>
                <upnp:class>object.item.audioItem.musicTrack</upnp:class>
                <res protocolInfo="http-get:*:audio/mpeg:*" size="20000">
                    http://10.1.1.1/Would.mp3
                </res>
        </item>
</DIDL-Lite>
```

FIG. 5A

```
GET /A2.MPEG_PS_NTSC HTTP/1.1
HOST:10.1.1.1:9001
getcontentFeature.dlna.org:1
TimeSeekRange.dlna.org:npt=0.00-
Request range: 0 - -1 msec
```

FIG. 5B

```
HTTP/1.1 200 OK
Server: Samsung HTTP streaming server
Content-Type: video/mpeg
Content-Length: 34339955
Cache-Control: no-cache
contentFeatures.dlna.org: DLNA.ORG_PN=MPEG_PS_NTSC;DLNA.ORG_OP=11
```

FIG. 7

```
<DIDL-Lite
xmlns:dc="http://purl.org/dc/elements/1.1/"
xmlns:upnp="urn:schemas-upnp-org:metadata-1-0/upnp/"
xmlns="urn:schemas-upnp-org:metadata-1-0/DIDL-Lite/">
    <item id="5" parentID="3" restricted="false">
        <dc:title>Would</dc:title>
        <dc:creator>Alice In Chains</dc:creator>
        <upnp:class>object.item.audioItem.musicTrack</upnp:class>
        <res protocolInfo="http-get:*:audio/mpeg:*" size="20000">
            http://10.1.1.1/RSS/control.cgi?action=192.10.10.1/Would.mp3
        </res>
    </item>
</DIDL-Lite>
```

CONTENT MANAGEMENT METHOD AND APPARATUS

CROSS-REFERENCE TO RELATED PATENT APPLICATION

This application claims priority from Korean Patent Application No. 10-2006-0065900, filed on Jul. 13, 2006, in the Korean Intellectual Property Office, the disclosure of which is incorporated herein in its entirety by reference.

BACKGROUND OF THE INVENTION

1. Field of the Invention

Methods and apparatuses consistent with the present invention relate to content management, and more particularly, to providing content to a device, which cannot directly use content provided by a content server.

2. Description of the Related Art

Really Simple Syndication (RSS) is an eXtensible Markup Language (XML)-based simple content syndication protocol. For example, if a user writes on his/her blog, an updated list is automatically created, resulting in an XML document, which is an RSS feed. Since an XML document created according to an RSS protocol includes information about a blog related to the XML document, a user who wants to read an article in the blog can collect update information of the blog without visiting a specific site by reading the created XML document using an RSS reader. That is, a user can receive the latest information of a favorite blog only if the user registers an RSS feed Uniform Resource Locator (URL) of the favorite blog in an RSS reader program. Although a blog is illustrated, a user can receive all content information of a site, which provides an RSS service, using an RSS feed without visiting the site.

Media RSS, which is obtained by extending an RSS protocol, has been suggested to syndicate various types of media, such as TV and video clips and movies, besides audio files and images provided through RSS. Podcast is a representative media syndication using Media RSS.

FIG. 1 is a signaling diagram illustrating a method of syndicating content using RSS.

Referring to FIG. 1, content syndication using RSS is performed between an RSS server 11, an RSS client 12 in which an RSS reader is included, and a mobile device 13 using syndicated content. The mobile device 13 is a device used when content is reproduced in a separate device instead of the RSS client 12.

In operation 101, a user subscribes for content provided by the RSS server 11 using an RSS reader program. As described above, the user can simply subscribe for the content by inputting an RSS feed URL into the RSS reader of the RSS client 12. In general, a personal computer (PC) driving the RSS reader program corresponds to the RSS client 12.

In operation 102, the RSS server 11 provides a list of content stored therein to the RSS client 12 using an XML document, and the RSS client 12 downloads the content requested by the user.

In operation 103, the user can reproduce the content using the mobile device 13 instead of the RSS client 12 by transmitting the downloaded content to a separate content player, such as the mobile device 13. For example, the user can transmit an MP3 audio file to a miniaturized MP3 player using the PC and reproduce the MP3 audio file using the miniaturized MP3 player.

In operation 104, the RSS reader of the RSS client 12 checks whether the content in the RSS server 11 is updated, i.e., whether new content exists.

In operation 105, the RSS client 12 searches the content list of the RSS server 11. If new content exists, the RSS client 12 downloads the new content using the RSS reader, and in operation 106, the RSS client 12 transmits the new content to the mobile device 13 so that the mobile device 13 can reproduce the new content.

As illustrated in FIG. 1, in order for the user to use the content provided by the RSS server 11, the RSS client 12 in which the RSS reader is included is necessary, and a device, such as the mobile device 13, for receiving content from the RSS client 12 is necessary.

Thus, a method of providing content of a specific server, such as the RSS server 11, to devices, which cannot directly use the content provided by the specific server, is required. In particular, when content can be shared with devices in home by connecting the devices to each other via a single network, e.g., using Digital Living Network Alliance (DLNA), a method of sharing content provided by a content server outside of the home network with the devices belonging to the home network is required.

SUMMARY OF THE INVENTION

The present invention provides a method and apparatus for providing content to a device, which cannot directly use content provided by a content server.

The present invention also provides a computer readable recording medium storing a computer readable program for executing the method.

According to an aspect of the present invention, there is provided a method for a first device to provide content to a second device in a home network, the method comprising: receiving content information through a Really Simple Syndication (RSS) feed provided from a content server outside of the home network; updating a content list, which can be provided by the first device through the home network, based on the content information which is received; and transmitting the updated content list to the second device.

The content list may be a Content Directory Service (CDS) content list according to a Universal Plug and Display (UPNP) Audio/Video (AV) architecture.

The method may further comprise: receiving a message from the second device requesting transmission of content; receiving the content which is requested from the content server based on URL information of the content included in the request message; and transmitting the content which is received to the second device.

The method may further comprise: if the content list is changed during the updating of the content list, receiving updated content from the content server; receiving a message requesting transmission of the updated content from the second device; and transmitting the updated content to the second device in response to the request message.

According to another aspect of the present invention, there is provided an apparatus for a first device to provide content to a second device in a home network, the apparatus comprising: a content information receiver which receives content information through an RSS feed which is provided from a content server outside of the home network; a content list update unit which updates a content list, which can be provided by the first device through the home network, based on the content information which is received; and a content list transmitter which transmits the updated content list to the second device.

The content list may be a CDS content list according to a UPNP AV architecture.

The apparatus may further comprise: a content receiver which receives content from the content server; a content transmission request receiver which receives a message requesting for transmission of requested content from the second device; and a content transmitter which transmits the requested content to the second device in response to the request message.

According to another aspect of the present invention, there is provided a computer readable recording medium storing a computer readable program for executing a method for a first device to provide content to a second device in a home network, the method comprising: receiving content information through an RSS feed provided from a content server outside of the home network; updating content list, which can be provided by the first device through the home network, based on the content information which is received; and transmitting the updated content list to the second device.

BRIEF DESCRIPTION OF THE DRAWINGS

FIG. 3 illustrates an RSS feed according to an exemplary embodiment of the present invention;

FIG. 4 illustrates a Content Directory Service (CDS) content list according to an exemplary embodiment of the present invention;

FIGS. 5A and 5B illustrate Hypertext Transfer Protocol (HTTP) headers according to an exemplary embodiment of the present invention;

FIG. 7 illustrates a CDS content list according to another exemplary embodiment of the present invention;

DETAILED DESCRIPTION OF EXEMPLARY EMBODIMENTS OF THE INVENTION

Figure 1:
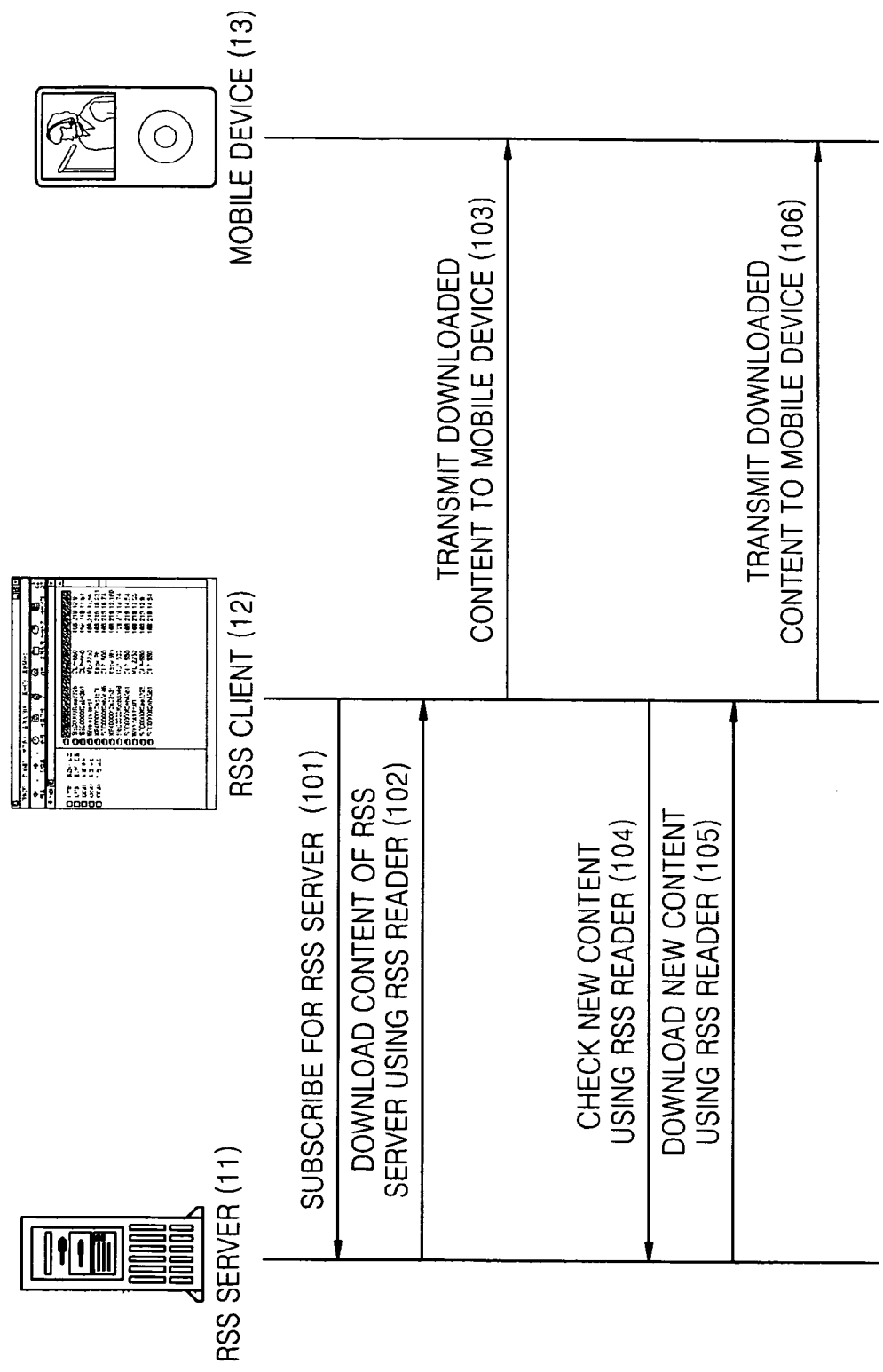
FIG. 1 is a signaling diagram illustrating a content syndication method.
Figure 2:
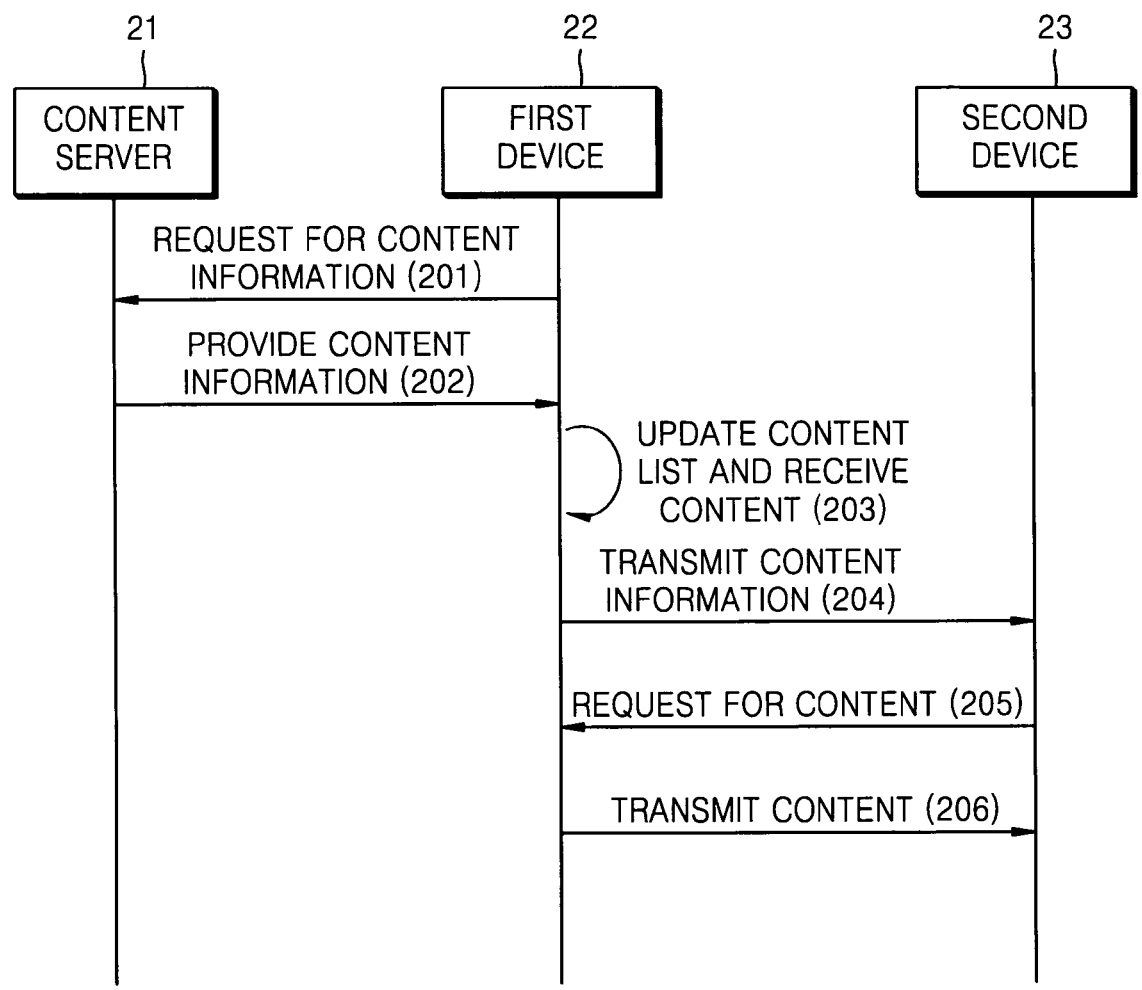
FIG. 2 is a signaling diagram illustrating a content providing method according to an exemplary embodiment of the present invention.

FIG. 2 is a signaling diagram illustrating a content providing method according to an exemplary embodiment of the present invention.

Referring to FIG. 2, the content providing method is performed by a content server 21, a first device 22, and a second device 23.

The content server 21 is a server possessing content to be finally provided to the second device 23, and the second device 23 is a network device, which receives content from the content server 21. Here, a case where the second device 23 cannot be directly connected to the content server 21 to receive content may exist. For example, there may exist a case where the content server 21 is an RSS server and can provide content to only a client in which an RSS reader is included, and the first device 22 and the second device 23 are network devices belonging to a home network such as a DLNA network. FIG. 2 illustrates a method for the first device 22 to provide content to the second device 23 when the first device 22 can receive content from the content server 21 since the first device 22 includes an RSS reader whereas the second device 23 cannot directly receive content from the content server 21 since the second device 23 does not include an RSS reader.

In operation 201, the first device 22 requests the content server 21 for information on content. The content information request can be simply performed by inputting a URL of an RSS feed of the content server 21 into the RSS reader included in the first device 22. The RSS feed is an XML document including information on metadata of content possessed by the content server 21 and is used to inform an RSS client of the information on content of the content server 21.

In operation 202, the first device 22 receives the information on content from the content server 21. The information on content is provided by receiving the RSS feed of the content server 21 and reading the RSS feed using the RSS reader included in the first device 22.

FIG. 3 illustrates the RSS feed provided by the content server 21 illustrated in FIG. 2, according to an exemplary embodiment of the present invention. A content URL and name illustrated in FIG. 3 are arbitrary.

Referring to FIG. 3, the RSS feed includes the information on content possessed by the content server 21, i.e., an RSS server. An enclosure tag is a URL of the content possessed by the content server 21 and contains "http://vod/rssinfo.meg2" and information on a length and type of the content.

Referring back to FIG. 2, in operation 203, the first device 22 updates a list of content to be transmitted to the second device 23 based on the RSS feed transmitted from the content server 21. The content list includes information on content which the first device 22 can provide to the second device 23. The content list update is achieved by adding information on new content included in the RSS feed provided by the content server 21 to the content list.

Since the first device 22 and the second device 23 are connected to each other via the home network as described above, the first device 22 updates the content list according to a method of sharing content in the home network. If the home network is a UPNP network, the first device 22 updates a CDS content list of a UPNP AV architecture.

When the content list is updated, the content is also received. If new content exists in the content server 21 by referring to the RSS feed, the first device 22 receives the new content and stores in a database included therein. The first device 22 requests the content server 21 for content using a method, such as an HTTP GET method, and receives and stores the content.

In operation 204, the first device 22 transmits content information to the second device 23. If the first device 22 and the second device 23 are connected to each other via the DLNA network as described above, the first device 22 transmits information on content through CDS in the UPnP network.

In this case, the second device 23 transmits a 'CDS: Browse( )' instruction to the first device 22 through a Control Point (CP) of the DLNA network, and the first device 22 transmits an XML document including metadata of the content to the second device 23 in response to the 'CDS:Browse( )' instruction.

FIG. 4 illustrates a CDS content list transmitted to the second device 23 by the first device 22, according to an exemplary embodiment of the present invention. A device URL and name illustrated in FIG. 4 are arbitrary.

Referring to FIG. 4, the content list transmitted by the first device 22 in operation 204 of FIG. 2 includes URL information of the content stored in the first device 22. Since the content possessed by the content server 21 is transmitted to and stored in the first device 22 in operation 203 of FIG. 2, the URL information of the content stored in the first device 22 is included in the content list regardless of a URL of the content server 21. For example, if a URL of the first device 22 is 'http://10.1.1.1/' and a file name of the content received from the content server 21 and stored is 'Would.mp3', the content list transmitted to the second device 23 includes 'http://10.1.1.1/Would.mp3' as URL information of the content stored in the first device 22.

Referring back to FIG. 2, in operation 205, the second device 23 requests the first device 22 for transmission of content. That is, the second device 23 transmits a request message including URL information of content to be received by the first device 22 based on the URL information of content, which has been transmitted through the CDS in operation 204. If the first device 22 and the second device 23 are network devices in a DLNA network, the request message is created using HTTP and transmitted to the first device 22.

As illustrated in FIGS. 5A and 5B, the DLNA prescribes articles, which must be added to an HTTP header when media content is requested and received in response to the request. However, when information on content is transmitted to the second device 23 through the CDS of the first device 22, the requisite articles prescribed in the DLNA may not be included in the HTTP header.

Thus, as illustrated in FIG. 5A, when the second device 23 creates a request message using HTTP in order to request the first device 22 for content, the second device 23 can create the request message including a message for requesting the requisite articles. Here, the requisite articles correspond to 'getcontentFeature.dlna.org' and 'TimeSeekRange.dlna.org' prescribed in a DLNA guideline, wherein 'TimeSeekRange.dlna.org' is an article needed to perform a function of seeking content provided in a DLNA network.

In operation 206, the first device 22 transmits the requested content to the second device 23 in response to the content transmission request of the second device 23, which has been received in operation 205. That is, the content transmitted from the content server 21 to the first device 22 via the RSS is transmitted to the second device 23 via the first device 22.

As illustrated in FIG. 5B, if the first device 22 and the second device 23 are network devices in a DLNA network, media content is transmitted using HTTP as in operation 205. As described above, in this case, predetermined requisite articles must be included in an HTTP header, wherein the requisite articles correspond to 'Content-type', 'Contentlength', 'contentFeatures.dlna.org' and 'TimeSeekRange.dlna.org' prescribed in the DLNA guideline. If the requisite articles are not included in the content information provided by the content server 21, the first device 22 creates the requisite articles and transmits the created requisite articles to the second device 23. In this case, the first device 22 creates the requisite articles by extracting information on content by analyzing the received content and combining the extracted information with the content information received from the content server 21.

Figure 6:
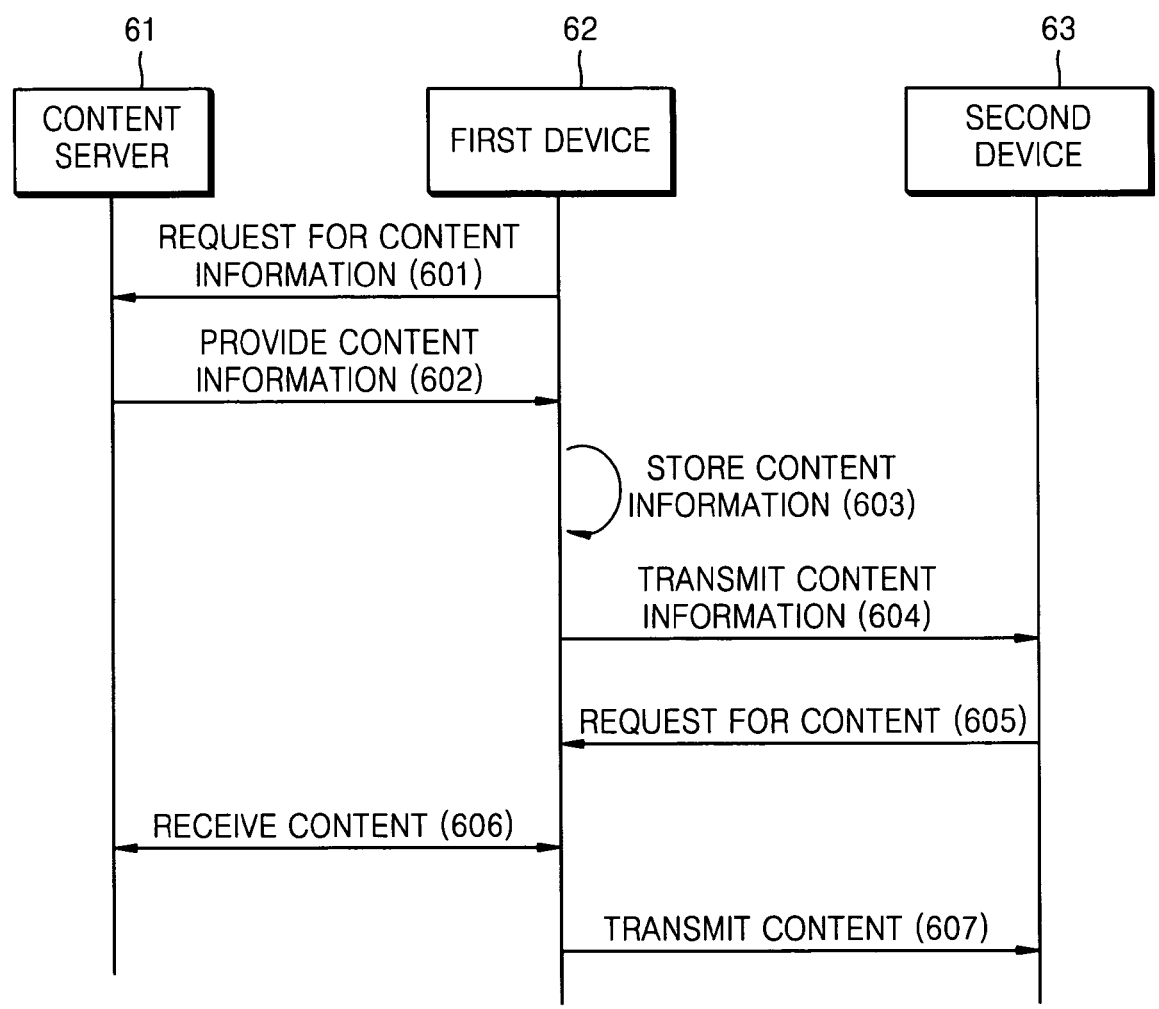
FIG. 6 is a signaling diagram illustrating a content providing method according to another exemplary embodiment of the present invention.

FIG. 6 is a signaling diagram illustrating a content providing method according to another exemplary embodiment of the present invention.

Like the content providing method illustrated in FIG. 2, a content server 61 is a server possessing content to be finally provided to a second device 63, and the second device 63 is a network device, which receives content from the content server 61. Here, a case where the second device 63 cannot be directly connected to the content server 61 to receive content may exist. For example, if the content server 61 is an RSS server and can provide content to only a client in which an RSS reader is included, and if a first device 62 and the second device 63 are network devices belonging to a home network such as a DLNA network, the second device 63 cannot directly request the content server 61 for content and receive the content.

In operation 601, the first device 62 requests the content server 61 for information on content. If the content server 61 is an RSS server, the content information request can be simply performed by inputting a URL of an RSS feed of the content server 61 into the RSS reader included in the first device 62. The RSS feed is an XML document including information on metadata of content possessed by the content server 61 and is used to inform the first device 62 of a content list of the content server 61.

In operation 602, the first device 62 receives the information on content from the content server 61. If the content server 61 is an RSS server, the information on content is provided by reading the RSS feed of the content server 61 using the RSS reader included in the first device 62.

In operation 603, the first device 62 updates a list of content to be transmitted to the second device 63 based on the RSS feed transmitted from the content server 61. In order for the second device 63 to finally receive content, the first device 62 must inform the second device 63 of information on the content. Thus, the first device 62 updates a CDS content list of a network according to a UPnP architecture based on the content information received through the RSS feed.

Operation 603 is different from operation 203 in that the first device 62 receives only the information on content and the content exists in the content server 61 and is not transmitted to the first device 62. If the content provided by the content server 61 is content for only streaming, such as a voice or video stream, the first device 62 does not receive the content.

In operation 604, the first device 62 transmits content information to the second device 63. Since the first device 62 and the second device 63 are connected to each other via the DLNA network as described above, the first device 62 transmits information on content through CDS in the UPNP network.

In this case, the second device 63 transmits a 'CDS:Browse( )' instruction to the first device 62 through a CP of the DLNA network, and the first device 62 transmits an XML document including metadata of the content to the second device 63 in response to the 'CDS:Browse( )' instruction.

FIG. 7 illustrates a CDS content list transmitted to the second device 63 by the first device 62, according to another exemplary embodiment of the present invention. A URL of the content server 61 and a URL and name of the first device 62 illustrated in FIG. 7 are arbitrary.

Referring to FIG. 7, unlike FIG. 4, URL information of the content stored in an XML document is a URL of the content stored in the content server 61. It is assumed that the URL of the content server 61 is 'http://192.10.10.1/', a URL of the first device 62 is 'http://10.1.1.1/', and a file name of the content stored in the content server 61 is 'Would.mp3'. In an XML document transmitted to the second device 63, '192.10.10.1/Would.mp3' is included as URL information of the content stored in the content server 61. However, since the content is transmitted to the second device 63 via the first device 62, when the first device 62 transmits the information on the content to the second device 63, URL information of the first device 62 is included such as 'http://10.1.1.1/RSS/control.cgi?action=192.10.10.1/Would.mp3/'.

In operation 605, the second device 63 requests the first device 62 for transmission of content. That is, the second device 63 transmits a request message including URL information of content to be received to the first device 62 based on the URL information of content, which has been transmitted through the XML document in operation 604. Since the first device 22 and the second device 23 are network devices in the DLNA network, the request message is created using HTTP and transmitted to the first device 62.

As in operation 205 of FIG. 2, a request for articles, which must be added to an HTTP header in order to request media content and receive the content in response to the request is also performed.

In operation 606, the first device 62 receives the content from the content server 61. That is, the first device 62 requests the content server 61 for the content based on the URL information included in the content request message, which has been received from the second device 63 in operation 605, and receives the content.

In operation 607, the first device 62 transmits the content, which has been received from the content server 61 in operation 606, to the second device 63. In this case, as in operation 206 of FIG. 2, predetermined requisite articles prescribed in the DLNA guideline are transmitted with the content. As described in operation 206 of FIG. 2, if the requisite articles are not included in the content information provided by the content server 61, the first device 62 creates the requisite articles and transmits the created requisite articles to the second device 63. That is, the first device 62 creates the requisite articles by extracting information on content by analyzing the received content and combining the extracted information with the content information received from the content server 61.

Figure 8:
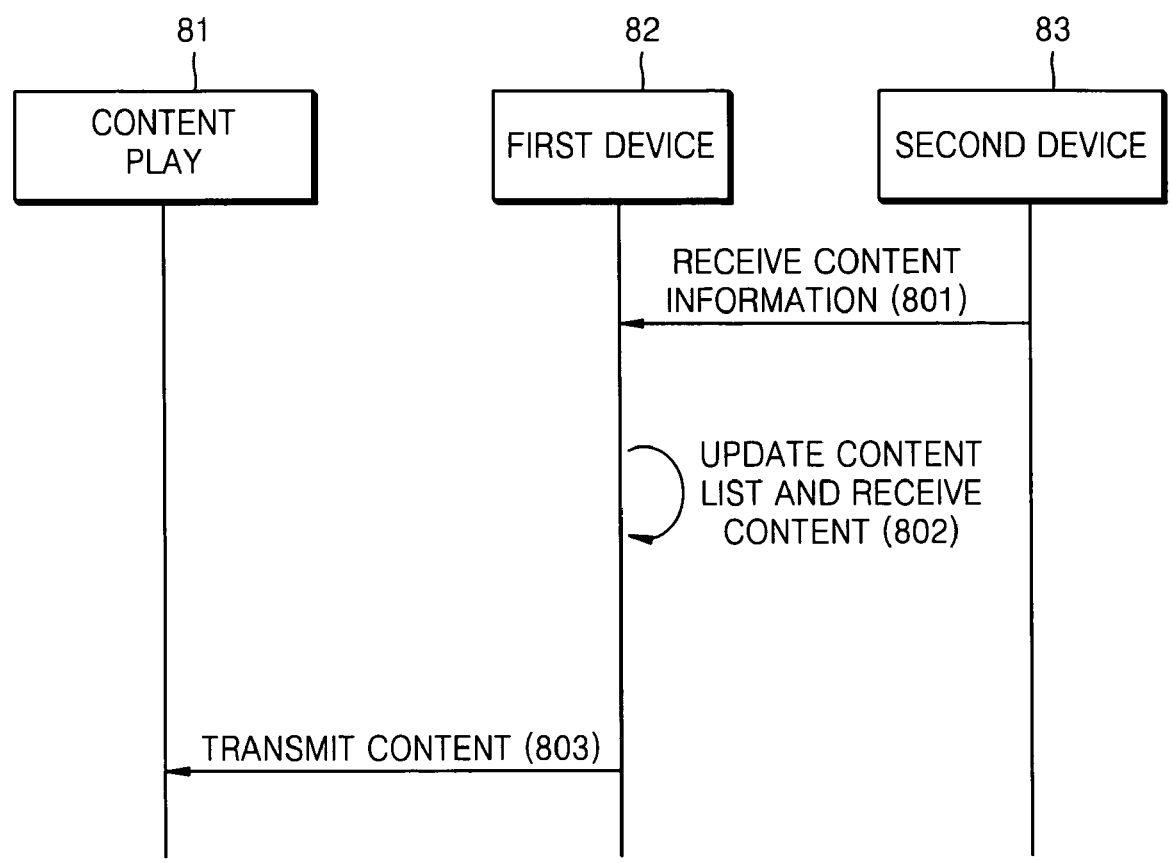
FIG. 8 is a signaling diagram illustrating a content providing method according to another exemplary embodiment of the present invention.

FIG. 8 is a signaling diagram illustrating a content providing method according to another exemplary embodiment of the present invention.

A second device 83 is a server possessing content to be finally provided to a content reproduction device 81, and the content reproduction device 81 is a network device, which receives content from the second device 83. Here, a case where the content reproduction device 81 cannot be directly connected to the second device 83 to receive content may exist. If a first device 82 and the second device 83 are network devices belonging to a home network such as a DLNA network, and if the content reproduction device 81 is not a DLNA network device but a device, which receives content through RSS, the content reproduction device 81 cannot directly receive content provided by the second device 83 via the DLNA network. FIG. 8 illustrates a method for the content reproduction device 81 to receive content provided by the second device 83 via the first device 82.

Referring to FIG. 8, in operation 801, the first device 82 receives information on content from the second device 83. Since the first device 82 and the second device 83 are connected to each other via the DLNA network, the first device 82 receives the information on content through CDS in the UPNP network.

In this case, the first device 82 transmits a 'CDS:Browse( )' instruction to the second device 83 through a CP of the DLNA network, and the second device 83 transmits an XML document including metadata of the content to the first device 82 in response to the 'CDS:Browse( )' instruction.

In operation 802, the first device 82 updates a list of content to be transmitted to the content reproduction device 81 based on the content information, which has been received in operation 801. If the content reproduction device 81 is an RSS device, which can receive content through an RSS reader, the first device 82 updates the content list of an RSS reader included therein. The updated content list is displayed to a user of the first device 82 through the RSS reader.

When the content list is updated, the first device 82 also receives content to be transmitted to the content reproduction device 81 from the second device 83. If the first device 82 and the second device 83 are network devices in the DLNA network, the first device 82 receives the content using HTTP.

In operation 803, content stored in the first device 82 is transmitted to the content reproduction device 81 by a user's selection. That is, the content list of the RSS reader included in the first device 82 is displayed to the user, and content selected by the user is transmitted to the content reproduction device 81. Thus, the content reproduction device 81, which cannot be directly connected to the second device 83 in order to receive content, uses the content via the first device 82.

Figure 9:
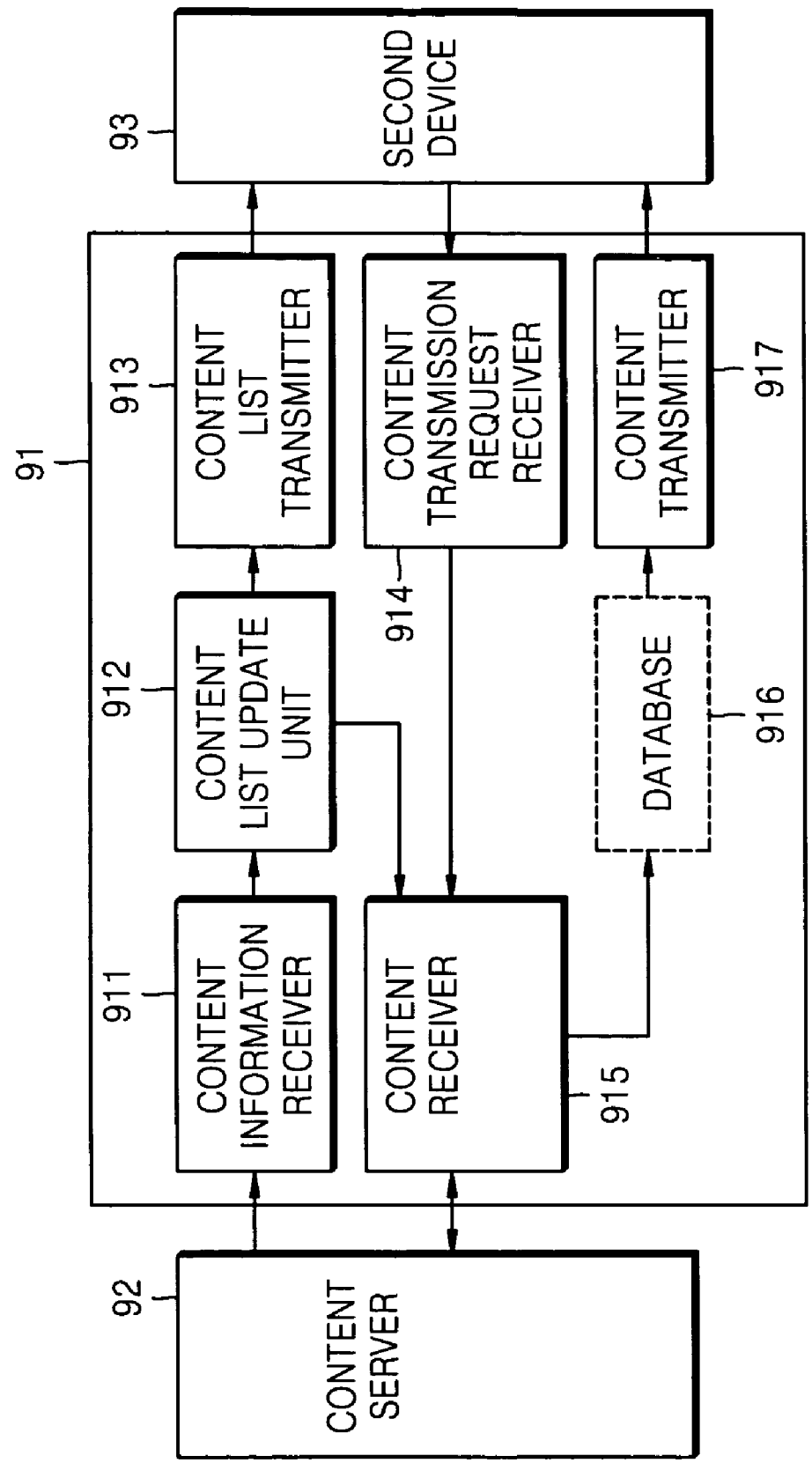
FIG. 9 is a block diagram of a content providing apparatus according to an exemplary embodiment of the present invention.

FIG. 9 is a block diagram of a content providing apparatus 91 according to an exemplary embodiment of the present invention.

Referring to FIG. 9, the content providing apparatus 91 of a first device (referred to as 22 or 62) includes a content information receiver 911, a content list update unit 912, a content list transmitter 913, a content transmission request receiver 914, a content receiver 915, a database 916, and a content transmitter 917.

The content information receiver 911 receives information on content from a content server 92. The information on content is received through an RSS feed provided by the content server 92.

The content list update unit 912 updates a list of content to be transmitted to a second device 93, which belongs to a home network with the first device (referred to as 22 or 62), based on the content information received by the content information receiver 911.

The content list transmitter 913 transmits the content list updated by the content list update unit 912 to the second device 93. If the home network is a DLNA network, the content list transmitter 913 transmits a CDS content list to the second device 93 in response to a CDS request message received from the second device 93 through a DLNA CP.

The content transmission request receiver 914 receives a content transmission request message from the second device 93. That is, the content transmission request receiver 914 receives a content transmission request message, which is transmitted from the second device 93 based on the content list transmitted from the content list transmitter 913.

The content receiver 915 receives content from the content server 92 based on the content transmission request message received by the content transmission request receiver 914. The content is received using a method such as an HTTP SET method. Here, content can be received only if a content transmission request message is received by the content transmission request receiver 914, or content, which is newly added to a content list, can be received from the content server 92 if the content list update unit 912 updates the content list regardless of whether content transmission is requested.

The database 916 is a component needed if content is received from the content server 92, stored in the first device (referred to as 22 or 62), and provided to the second device 93. If the content provided by the content server 92 does not have to be stored since the content is a stream for a streaming service, the database 916 is selectable.

The content transmitter 917 transmits the content stored in the database 916 to the second device 93. If the content is not stored in the database 916, the content received by the content receiver 915 is transmitted to the second device 93. If the first device (referred to as 22 or 62) and the second device 93 are devices in the DLNA network, information on requisite articles necessary to transmit media content in the DLNA network is included in an HTTP header as described above.

Figure 10:
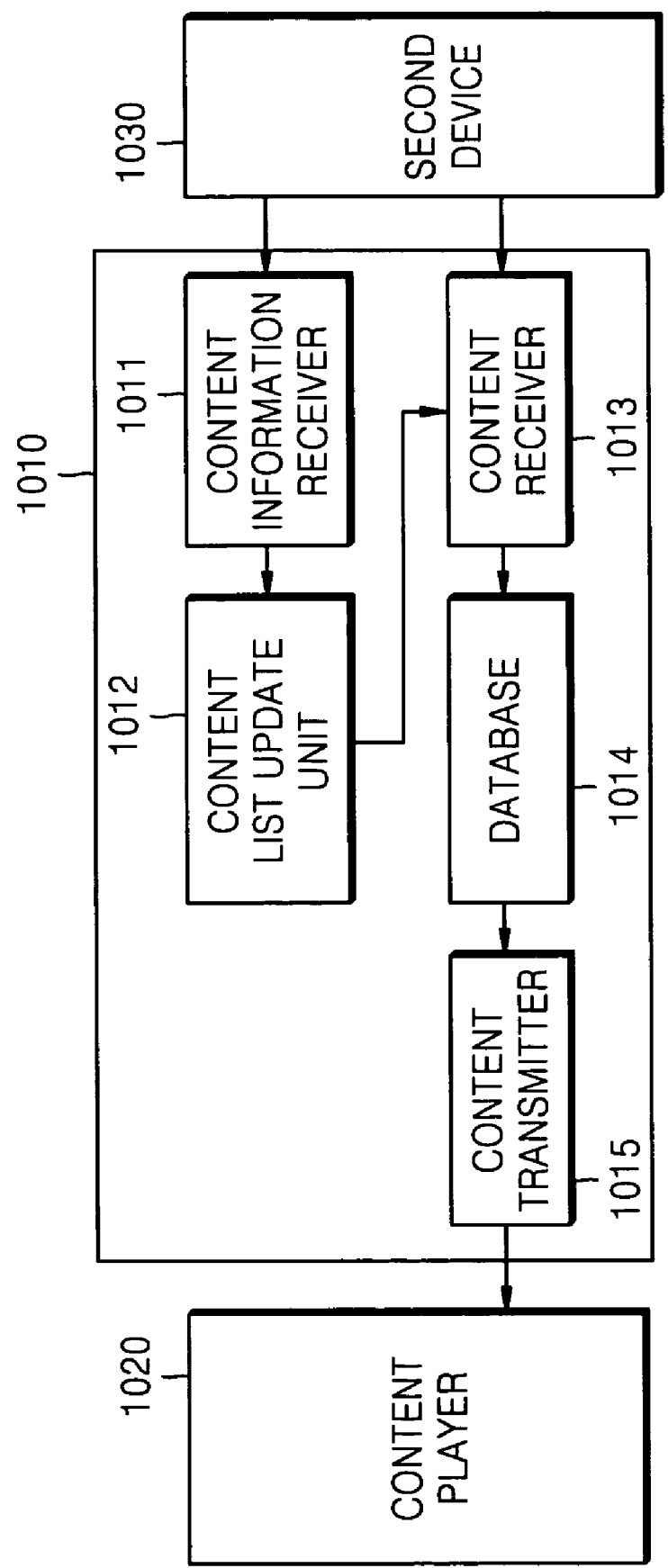
FIG. 10 is a block diagram of a content providing apparatus according to another exemplary embodiment of the present invention.

FIG. 10 is a block diagram of a content providing apparatus 1010 according to another exemplary embodiment of the present invention.

Referring to FIG. 10, the content providing apparatus 1010 of a first device (referred to as 82) includes a content information receiver 1011, a content list update unit 1012, a content receiver 1013, a database 1014, and a content transmitter 1015.

The content information receiver 1011 receives information on content from a second device 1030. If the first device (referred to as 82) and the second device 1030 are DLNA network devices, the information on content is received by the first device (referred to as 82) requesting for a content list to be transmitted through a DLNA CP and the second device 1030 transmitting a CDS content list.

The content list update unit 1012 updates a list of content to be transmitted to a content reproduction device 1020 based on the content information received by the content information receiver 1011. If the content reproduction device 1020 is an RSS device, which can receive content from an RSS reader, the content list is updated by updating a content list of an RSS reader included in the first device (referred to as 82).

The content receiver 1013 receives content from the second device 1030. That is, content newly added to the content list when the content list is updated is received from the second device 1030. The received content is stored in the database 1014 and selectively transmitted from content transmitter 1015 to the content reproduction device 1020 according to a user's selection.

The invention can also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage devices. The computer readable recording medium can also be distributed over network coupled computer systems so that the computer readable code is stored and executed in a distributed fashion.

As described above, according to the exemplary embodiments of the present invention, since a client, which cannot be directly connected to a content server in order to receive content, can receive the content via another device belonging to the same network, content sharing is maximized.

While the present invention has been particularly shown and described with reference to exemplary embodiments thereof, it will be understood by those of ordinary skill in the art that various changes in form and detail may be made therein without departing from the spirit and scope of the present invention as defined by the following claims.

What is claimed is:

1. An apparatus for a first device to provide content to a second device in a home network, the apparatus comprising:
   a content information receiver which receives content information through a Really Simple Syndication (RSS) feed which is provided from a content server outside of the home network;
   a content list update unit which updates a content list, which can be provided by the first device through the home network, based on the content information which is received; and
   a content list transmitter which transmits the updated content list to the second device,
   wherein the content list comprises Uniform Resource Locator (URL) information of the content, which is stored in the content server, and URL information of the first device so that the first device can receive the content from the content server and transmit the content which is received to the second device.

2. The apparatus of claim 1, wherein the content list is a Content Directory Service (CDS) content list according to a Universal Plug and Play (UPnP) Audio/Video (AV) architecture.

3. The apparatus of claim 2, further comprising:
   a content receiver which receives content from the content server;
   a content transmission request receiver which receives a message requesting transmission of requested content from the second device; and
   a content transmitter which transmits the requested content to the second device in response to the request message.

4. The apparatus of claim 3, wherein the home network is a home network according to a Digital Living Network Alliance (DLNA) guideline.

5. The apparatus of claim 4, wherein the content transmitter transmits the content together with requisite information needed to transmit media content according to the DLNA guideline.

6. A method for a first device to provide content to a second device in a home network, the method comprising:
   receiving content information through a Really Simple Syndication (RSS) feed provided from a content server outside of the home network;
   updating a content list, which can be provided by the first device through the home network, based on the content information which is received; and
   transmitting the updated content list to the second device,
   wherein the content list comprises Uniform Resource Locator (URL) information of the content, which is stored in the content server, and URL information of the first device so that the first device can receive the content from the content server and transmit the content which is received to the second device.

7. The method of claim 6, wherein the content list is a Content Directory Service (CDS) content list according to a Universal Plug and Play (UPnP) Audio/Video (AV) architecture.

8. The method of claim 7, further comprising:
   if the content list is changed during the updating of the content list, receiving updated content from the content server;
   receiving a message of transmission of the updated content from the second device; and
   transmitting the updated content to the second device in response to the request message.

9. The method of claim 8, wherein the content list comprises Uniform Resource Locator (URL) information of content which is stored in the first device after the first device receives the content from the content server.

10. The method of claim 7, further comprising:
    receiving from the second device a message requesting transmission of content;
    receiving the content which is requested from the content server based on the URL information of the content included in the request message; and
    transmitting the content which is received to the second device.

11. The method of claim 6, wherein the home network is a home network according to a Digital Living Network Alliance (DLNA) guideline.

12. The method of claim 11, wherein the transmitting of the received content comprises transmitting requisite information needed to transmit media content according to the DLNA guideline.

13. A computer readable storage medium storing a computer readable program for executing a method for a first device to provide content to a second device in a home network, the method comprising:

receiving content information through a Really Simple Syndication (RSS) feed provided from a content server outside of the home network;

updating a content list, which can be provided by the first device through the home network, based on the content information which is received; and transmitting the updated content list to the second device, wherein the content list comprises Uniform Resource Locator (URL) information of the content, which is stored in the content server, and URL information of the first device so that the first device can receive the content from the content server and transmit the content which is received to the second device.

* * * * *